(12) United States Patent
Zeng et al.

(10) Patent No.: US 9,668,664 B2
(45) Date of Patent: Jun. 6, 2017

(54) FOCAL POINT IDENTIFICATION AND MAPPING

(71) Applicant: CARDIOINSIGHT TECHNOLOGIES, INC., Cleveland, OH (US)

(72) Inventors: Qingguo Zeng, Solon, OH (US); Remi Dubois, Paris (FR); Ping Jia, Solon, OH (US); Ryan Bokan, Lakewood, OH (US); Venkatesh Vasudevan, Beachwood, OH (US); Charulatha Ramanathan, Solon, OH (US); Maria Strom, Moreland Hills, OH (US); Brian P. George, Medina, OH (US)

(73) Assignee: Cardioinsight Technologies, Inc., Cleveland, OH (US)

( * ) Notice: Subject to any disclaimer, the term of this patent is extended or adjusted under 35 U.S.C. 154(b) by 0 days.

(21) Appl. No.: 14/156,903

(22) Filed: Jan. 16, 2014

(65) Prior Publication Data

US 2014/0200473 A1 Jul. 17, 2014

Related U.S. Application Data

(60) Provisional application No. 61/753,753, filed on Jan. 17, 2013.

(51) Int. Cl.
*A61B 5/044* (2006.01)
*A61B 5/04* (2006.01)
(Continued)

(52) U.S. Cl.
CPC ........ *A61B 5/04012* (2013.01); *A61B 5/0044* (2013.01); *A61B 5/044* (2013.01);
(Continued)

(58) Field of Classification Search
CPC . A61B 5/04012; A61B 5/0044; A61B 5/0452; A61B 2576/023
See application file for complete search history.

(56) References Cited

U.S. PATENT DOCUMENTS

| 4,974,598 A | 12/1990 | John |
| 2007/0021679 A1* | 1/2007 | Narayan ............ A61B 5/04525 600/518 |

(Continued)

FOREIGN PATENT DOCUMENTS

| EP | 2266459 | 12/2010 |
| WO | 0045700 | 8/2000 |

(Continued)

OTHER PUBLICATIONS

International Search Report—3 pp., Nov. 9, 2014, CardioInsight Technologies, Inc.

(Continued)

*Primary Examiner* — George Evanisko
(74) *Attorney, Agent, or Firm* — Tarolli, Sundheim, Covell & Tummino LLP

(57) ABSTRACT

A method can determine one or more origins of focal activation. The method can include computing phase for the electrical signals at a plurality of nodes distributed across a geometric surface based on the electrical data across time. The method can determine whether or not a given candidate node of the plurality of nodes is a focal point based on the analyzing the computed phase and magnitude of the given candidate node. A graphical map can be generated to visualize focal points detected on the geometric surface.

24 Claims, 8 Drawing Sheets

(51) Int. Cl.
*A61B 5/00* (2006.01)
*A61N 1/36* (2006.01)
*A61B 5/0452* (2006.01)
*A61B 18/14* (2006.01)

(52) U.S. Cl.
CPC ................ *A61B 5/486* (2013.01); *A61N 1/36* (2013.01); *A61B 5/0452* (2013.01); *A61B 18/1492* (2013.01); *A61B 2576/023* (2013.01)

(56) References Cited

U.S. PATENT DOCUMENTS

| | | | |
|---|---|---|---|
| 2007/0038251 A1 | 2/2007 | Pachon Mateos | |
| 2009/0187097 A1* | 7/2009 | Saba | A61B 5/04012 600/424 |
| 2011/0251505 A1* | 10/2011 | Narayan | A61B 5/0422 600/515 |
| 2012/0157822 A1* | 6/2012 | van Dam | A61B 5/0402 600/411 |
| 2013/0274582 A1* | 10/2013 | Afonso | A61B 5/0422 600/374 |

FOREIGN PATENT DOCUMENTS

| | | |
|---|---|---|
| WO | 2006052838 | 5/2006 |
| WO | 2008138009 | 11/2008 |
| WO | 2012092016 | 7/2012 |

OTHER PUBLICATIONS

Written Report—9 pp., Nov. 9, 2014, CardoInsight Technologies, Inc.

Supplementary European Search Report, European Application No. 14741167, Applicant: CardioInsight Technologies Inc.; Date of Completion Jul. 21, 2016, 9 pgs.

\* cited by examiner

FOCAL POINT IDENTIFICATION AND MAPPING

RELATED APPLICATION

This application claims the benefit of U.S. Provisional Patent Application No. 61/753,753 filed Jan. 17, 2013 and entitled FOCAL POINT IDENTIFICATION AND MAPPING, the entire contents of which is incorporated herein by reference.

TECHNICAL FIELD

This disclosure relates to focal point identification and mapping.

BACKGROUND

Electrocardiographic mapping (ECM) is a technology that is used to determine and display heart electrical information from sensed electrical signals. Mapping of cardiac electrical activity can be important in the diagnosis of cardiac arrhythmia such as fibrillation, including atrial and ventricular fibrillation, as well as tachycardia, including atria tachycardia and ventricular tachycardia. In many arrhythmias, the origin of the aberrant beat is from a small region of abnormal or triggered activity that propagates from this point and results in abnormal activation of the heart. Detecting and visualizing this mechanism of arrhythmias can be relevant to the clinical diagnosis of arrhythmias.

SUMMARY

This disclosure relates to focal point identification and mapping.

An example can include a non-transitory computer-readable medium having instructions executable by a processor for performing a method. The method can include computing phase for signals of each of a plurality of nodes on a geometric surface region associated with tissue of a patient, a subset of the nodes surrounding a given node of the plurality of nodes defining neighboring nodes of the given node. The method can also include analyzing the computed phase of the given node relative to the phase of each of a set of neighboring nodes of the given node over an activation time period associated with the given node. The method can also include determining if the given node is a focal point based on the analyzing. The computing, analyzing and determining can be repeated for each node of at least a substantial portion of the plurality of nodes to provide focal point data specifying a spatial location corresponding to each detected focal point for the geometric surface region.

Another example can be directed to a system that includes memory to store data and machine readable instructions a processor to access the memory and execute the machine readable instructions. The machine readable instructions can include a phase calculator programmed to compute phase for electrical signals at a plurality of nodes distributed across a geometric surface corresponding to patient tissue. The instructions can also include a focal detector programmed to determine whether or not a given candidate node of the plurality of nodes is a focal point based on the analyzing the computed phase of the given candidate node relative to the phase of each node in a set of nodes neighboring the given node for an activation time interval associated with the given candidate node, focal point data being stored in the memory based on the determination by the focal detector. The instructions can also include a map generator programmed to generate a graphical map representing focal points detected on the geometric surface based on the focal point data.

As another example a method can include storing, in memory, electrical data representing electrical signals for a geometric surface corresponding to patient tissue. A processor can compute phase for the electrical signals at a plurality of nodes distributed across the geometric surface based on the electrical data. A processor can further determine whether or not a given candidate node of the plurality of nodes is a focal point based on the analyzing the computed phase of the given candidate node relative to the phase of each node in a set of nodes neighboring the given node for an activation time interval associated with the given candidate node. Focal point data can be stored in the memory based on the determination. A graphical map can be provided to a display to visualize focal points detected on the geometric surface based on the focal point data.

DETAILED DESCRIPTION

Figure 1:
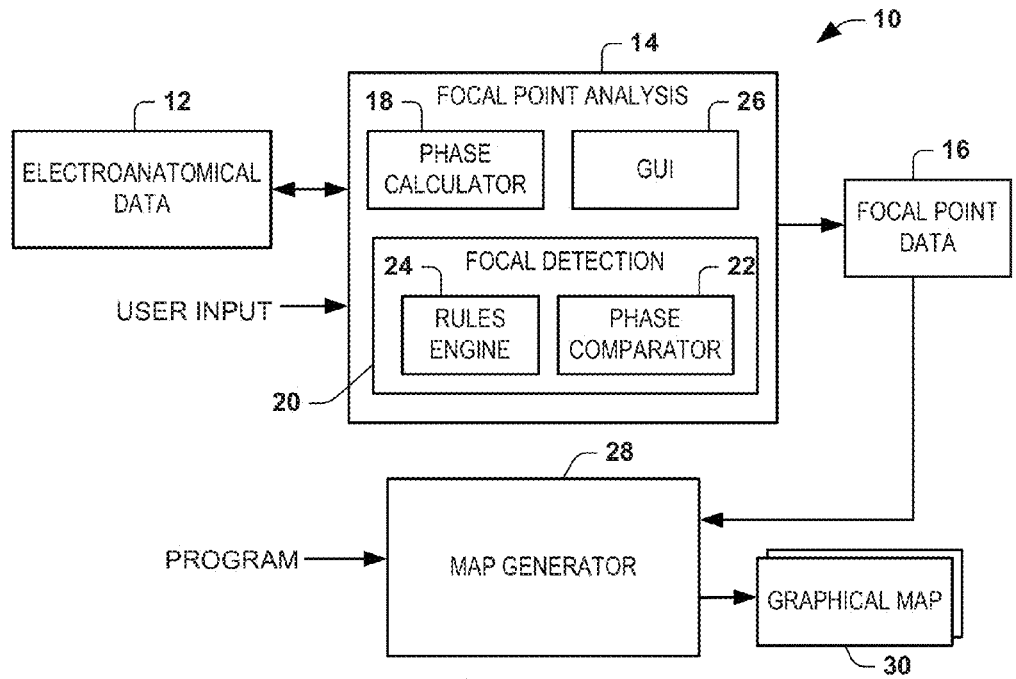
FIG. 1 depicts an example of a system to identify and map one or more focal points.

This disclosure relates to identifying one or more origins of focal electrical activity, such as arrhythmia. In several examples disclosed herein, the approach is described in relation to identifying a focal point (also referred to as an activation trigger or focal trigger) for atrial fibrillation; however, the approach can be applied to identify focal points of other types of cardiac activity including arrhythmias such as atrial tachycardia, ventricular fibrillation, ventricular tachycardia or the like. As disclosed herein, a focal point can thus refer to any point a location where an activation initiates and spreads out from such initial location to its surrounding tissue.

By way of example, systems and methods can identify focal points for a given geometric surface based on analysis spatial and temporal information related to activation and phase of signals for nodes across a geometrical surface. The analysis can include a comparison of a phase of node on the given geometric surface relative to the phase of nodes residing in a neighborhood (e.g., one or more layers of nodes) around the given node. The comparison can be made between the given node and its neighboring nodes over a time period sufficient to encompass a trigger event—corresponding to a focal point. For instance, neighbors of a focal point node have a later activation time, but are synchronized in phase with the focal point node. Scores can be assigned to each node based on comparisons. A corresponding focal point map can be generated based on the scores accumulated for each node.

As another example, the systems and methods can identify focal points for a given geometric surface by analyzing a set of one or more focal candidate nodes according to a spread of activation from an initial focal candidate node relative to surrounding nodes in a neighborhood (e.g., one or more layers) around the initial candidate node. Such systems and methods can apply rules to evaluate the spread of activation spatially and temporally to determine whether or not to classify the initial focal candidate node as a focal point.

The resulting focal point data can also be utilized to generate a graphical visualization to present spatially and temporally consistent information in the one or more maps (e.g., presented according to a color scale or grayscale. The spatial location of each identified focal point can be used as a clinical target for performing a therapy, such as disclosed herein (see, e.g., FIG. 11).

The systems and methods disclosed herein can be used as part of a diagnostic and/or treatment workflow to facilitate the identification and locating of fibrillation mechanisms based on electrical activity acquired for the patient. In some examples, the patient electrical activity can include non-invasive body surface measurements of body surface electrical activity. Additionally or alternatively, the patient electrical activity can include invasive measurements of heart electrical activity, including epicardial measurements and/or endocardial measurements.

FIG. 1 depicts an example of a system 10 to identify focal points on a geometric surface based on analysis of electroanatomic data (e.g., data describing electrical information in relation to anatomical structures) 12. The electroanatomic data 12 can be provided to characterize electrical activity for a geometric surface, such as tissue, of the patient (e.g., human or other animal). The electroanatomic data can be determined from non-invasively acquired electrophysiological signals, invasively acquired electrophysiological signals or a combination of non-invasive and invasive electrophysiological signals.

As disclosed herein, the electroanatomic data 12 can represent electrical activity for an anatomic structure of the patient, such as can include the heart, brain or other anatomic structures. For the example where the anatomic structure is the patient's heart, the electroanatomic data 12 can represent electrical information for a geometric surface corresponding to the heart, such as an epicardial surface, an endocardial surface or another cardiac envelope. The geometric surface can be patient specific (e.g., based on imaging data for the patient) or it can correspond to a generic model or it can be a hybrid model that is generated based on patient-specific data (e.g., imaging data, patient measurements and/or the like) and a generic anatomic model for the surface. Thus, the geometric surface need not correspond to an actual surface of the tissue but instead can represent a spatial construct associated with the electroanatomic data 12.

The system 10 can include a focal analysis module 14 that is programmed to generate focal point data 16 identifying one or more (or in some cases zero) focal points based on the electroanatomic data 12. The focal analysis module 14 can provide the focal point data 16 for at least a portion (e.g., a region of interest) and suitably the entire geometric surface. As disclosed herein, a focal point can correspond to a single node or a group of one or more contiguous nodes on the geometric surface.

The focal point analysis module 14 can include a phase calculator 18 to compute phase values for each of a plurality of nodes on a geometric surface (e.g., a spatial region of the heart) for a time interval or a plurality of time intervals. The approach used to compute the phases can vary depending on the type of electroanatomic data. The phase calculator 18 can be programmed to selectively implement a phase computation technique that can be selected from a predetermined list or be a user-specified calculation, such as in response to a user input. As one example, the phase calculator 18 can be programmed to compute phase according to the approach disclosed in PCT Application No. PCT/US13/60851 filed Sep. 20, 2013, and entitled PHYSIOLOGICAL MAPPING FOR ARRHYTHMIA, which is incorporated herein by reference. Phase could alternatively be computed by other approaches. The phase calculator 18 thus can compute the phase for each of the nodes on a geometric surface for a period of time (e.g., one or more time intervals). This time period can be set based on a user input or be a predetermined default amount of time.

The focal analysis module 14 includes a focal detection function 20 programmed to classify a given candidate node as a focal point or not a focal point based on the phase computed (e.g., by the phase calculator 18) for the given candidate node and each of its neighboring nodes in a corresponding interval. In the example of FIG. 1, the focal detection function 20 employs a phase comparator 22 and rules engine 24 to determine whether or not each candidate node is a focal point. The focal detection function 20 can make the determination for each candidate node and a set of its neighboring nodes, which can include a layered set of one or more neighbors. The definition of the number of layers can be stored as part of the rules engine 24, which can be fixed or programmable in response to a user input.

Figure 2:
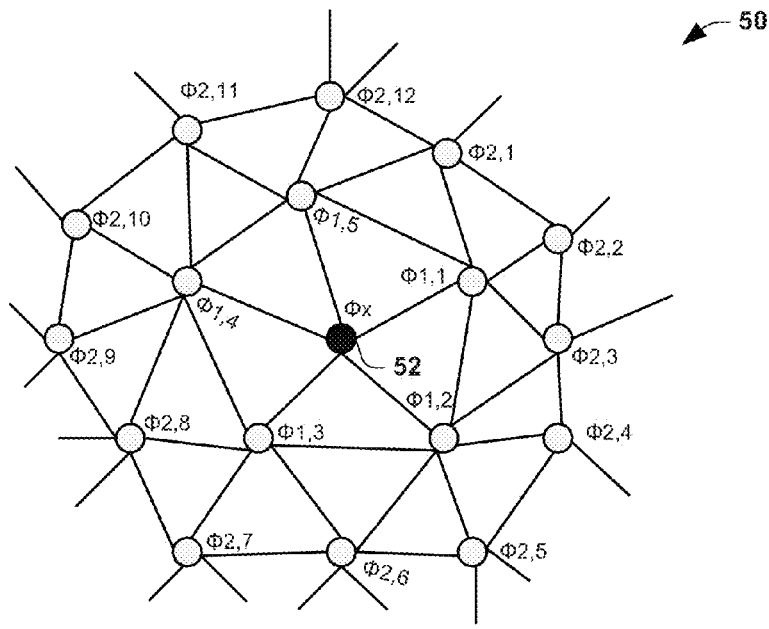
FIG. 2 depicts an example of a layered neighbor diagram that can be implemented for analyzing a selected vertex as a focal point.

As an example, FIG. 2 depicts a layered diagram 50 demonstrating an example of a neighborhood for a given candidate node 52. A subset of the nodes surrounding a given node 52 thus can define the given node's neighboring nodes. The neighboring nodes of the given node can include an arrangement of nodes having a plurality of layers that provide a multi-layer neighborhood of the nodes for the given node (e.g., the vertex) 52. Each respective layer around the given node can be defined based on spatial connectivity and/or spatial distance with respect to the given node. For example, a first layer of neighboring nodes can surround (e.g., circumscribe) just the given node 52. The nodes in the first layer can correspond to vertices with phases $\phi_{1,1}$, $\phi_{1,2}$, $\phi_{1,3}$, $\phi_{1,4}$, and $\phi_{1,5}$ (e.g., computed by the phase calculator 18). A next layer of the neighborhood 50 can include another subset of nodes that surround the first layer and the given node. The nodes in such second layer are represented as vertices with respective phases $\phi_{2,1}$, $\phi_{2,2}$, $\phi_{2,3}$, $\phi_{2,4}$, $\phi_{2,5}$, $\phi_{2,6}$, $\phi_{2,7}$, $\phi_{2,8}$, $\phi_{2,9}$, $\phi_{2,10}$, $\phi_{2,11}$ and $\phi_{2,12}$. There can be any number of layers, which further can be programmable in response to a user input (e.g., via a GUI 24), as disclosed herein.

Referring back to FIG. 1, the phase comparator 22 can compare the phase of the given node to the phase of each of the nodes in one or more layers as a function of time. The phase comparator 22 can assign a prescribed score to one of the given node and its neighboring node based on each comparison. The resulting score from the set of comparisons can be stored in memory for each node on geometric surface. As mentioned, the rules engine 24 can control the size (e.g., number of layers) of the neighborhood for each candidate node, which can be the same or vary across the geometric surface.

The rules engine 24 can also control the scoring that is implemented by the focal detection function 20, including by the phase comparator 22. For instance, a binary score can be used or a weighted score can be implemented depending on spatial and/or temporal characteristics between the nodes or phase values that are compared. In some examples, the score for each comparison can be a fixed value, such as binary value depending on the results of the phase comparison (e.g., 1 if candidate has a greater phase than its neighbor, otherwise 0). In other examples, the rules can be set to vary the computed score. For instance, the score can vary as a function of the distance between the given node and each respective node to which the comparison is being made. As another example, the score can vary depending on which layer the node resides to which the comparison is being made. The score can be accumulated based on all comparisons made for each candidate node. For example, the score assigned based on a first layer comparison can be greater than a comparison for a higher layer. The comparing and scoring can be repeated for at least a substantial portion of the nodes on the geometric surface (and suitably all nodes on the geometric surface) such that each of the nodes is assigned a score that provides an indication of a location of a least one focal point for the geometric surface.

By way of further example, from a mathematical definition, at a given time t, the phase comparator 22 can determine that a focal point occurs at the location x if $$\phi_x(t) > \phi_{l,i}(t), \forall l=1 \ldots n, i \in N_l(x), \quad (1)$$

where:
$\phi_x(t)$ is the phase value at vertex x at time t,
$\phi_{l,i}(t)$ is the phase value at the ith vertex in the lth layer of neighborhood,
n is an adjustable parameter to control number of layers, and
$N_l(x)$ is a set containing all vertices in the lth layer of neighborhood of vertex x, as demonstrated in the layered neighbor diagram of FIG. 2.

To make this process robust against noise, several layers (e.g., n=2 to n=4 or more) can be utilized. A focal trigger typically will last at least a few milliseconds. Accordingly, the inequality above shall hold for a few consecutive samples across a time interval.

$$\phi_x(t) > \phi_{l,i}(t), \forall l=1 \ldots n, i \in N_l(x), t=1 \ldots m \quad (2)$$

where m is an adjustable parameter to control the minimum duration of this event to classify a vertex to be a focal (e.g., m=5 ms).

The rules engine 24 thus can be configured to control m and n when implemented by the phase comparator 22 of the focal detection 20. As mentioned, the parameter m and n (as well as other rules) can be set in response to a user input.

The phase comparison based on (2) can be performed at the time of activation for node X and a post activation time period. The time period for which the comparison is evaluated following activation at X can be a fixed default time period or it may be user programmable. In some examples, a variable evaluation time period can be set to vary based on the number of layers being evaluated in the neighborhood of node X (e.g., a greater number of layers can employ a larger time period to accommodate for spread). As an example, the activation time for each node, including the given node X, can be determined based on a time derivative of the electrogram signal at X, such as may be the time of minimum slope for the electrogram at X or maximum absolute slope; although other activation time detection algorithms may be used.

To represent the focal detection result numerically, for each node detected as a focal point per (2) above, the phase comparator 22 can score a given node with 1, for multiple instances occurring at the same or different nodes, such that the focal point analysis module 14 can accumulate scores for each node. As a mathematical example, the focal point analysis module 14 can employ the phase comparator 22 to determine a score $F_x(t)$ for vertex x at a given sample time t, which can be represented as follows:

$$F_x(t) = \begin{cases} 1, \text{ if } \phi_x(k) > \phi_{l,i}(k), \forall l = 1 \ldots n, i \in N_l(x), k = t+1, \ldots, t+m \\ 0, \text{ otherwise} \end{cases} \quad (3)$$

The focal point analysis module 14 can further calculate an aggregate score over time, such as can be represented as follows:

$$CF_x = \sum_t F_x(t) \quad (4)$$

As a further example, the rules engine 24 can establish a variable scoring to be applied for each comparison. Thus, instead of scoring each comparison between a vertex node and a neighboring node to be 1 or 0, as mentioned above, comparisons between a vertex node and neighbors can vary as a function of distance between nodes being compared. For example, the score assigned to the node having the greater phase for each focal point comparison (e.g., by phase comparator 22) can be weighted with decreasing scores if the neighbor node is further from the vertex node. In some examples, the weighted score can be set for each layer or the score can be computed as a function of a distance computed between the respective nodes.

By way of an example, if a vertex at a given sampling time is detected as a trigger, i.e., $F_x(t)=1$, then the rules engine 24 can be programmed to score all its n layers of neighbors as:

$$F_{l,i}(t) = \begin{cases} \dfrac{n+1-l}{n+1}, \text{ if } i \in N_l(x), F_x(t) = 1 \\ 0, \text{ otherwise} \end{cases} \quad (5)$$

The above rule implemented by the focal detection function 20 operates to weight scores spatially (e.g., inversely proportional to distance from the candidate node. For instance, the rules implemented by equation (5) will provide a first neighborhood with score $$\dfrac{n}{n+1},$$

and provide the nth neighborhood with score $$\frac{1}{n+1}.$$

For an example where n=4, the scores are 0.8, 0.2 for $1^{st}$ and $4^{th}$ layer neighbors, respectively. The rules provided by this approach allow the focal point with score 1.0 standing out among its neighboring nodes. The accumulated scores for each respective node can be stored (e.g., in memory) as the focal point data 16.

The system 10 can include a map generator 28 programmed to generate one or more graphical maps 30 to represent one or more focal points for the geometric surface based on the focal point data 16. For example, the map generator 28 can be programmed to generate a graphical map in which the accumulated focal point scores for each of the nodes on the geometric surface are mapped to a corresponding scale visualized on three-dimensional surface (e.g., a cardiac surface). For instance, the graphical map 30 can be visualized on the geometric surface according to a given scale (e.g., color scale or grayscale) to depict the range of focal point scores. The scale can be set by the map generator 28 to accommodate the range of accumulated scores that have been assigned to the nodes on the geometric surface. The resulting map thus can be used to identify focal points on the geometric surface. As a further example, the map generator 34 can be programmed to present a plurality of the graphical maps 30 for different time intervals and/or different geometric surfaces.

Figure 3:
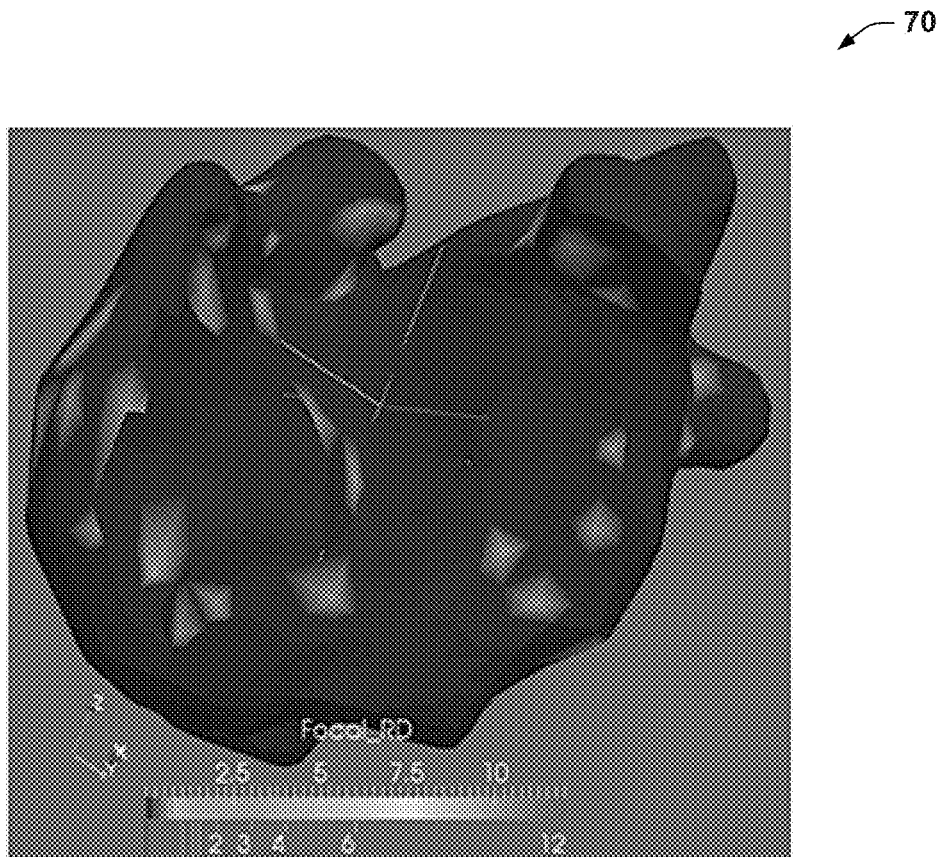
FIG. 3 depicts an example of a graphical map that can be generated to visually identify one or more focal points.

FIG. 3 depicts an example of focal map 70 that can be generated based on focal point data computed based on the systems and methods disclosed herein. In the example of FIG. 3, detected focal points are demonstrated as being distributed across the atria. In some cases, detecting focals based solely upon a neighborhood-based phase comparison, such as demonstrated in the example of FIG. 3, may yield false positive and/or false negative detections. Accordingly, the rules engine 24 can be programmed to apply additional rules (e.g., logic and/or controls) to help improve sensitivity and/or specificity.

Figure 4:
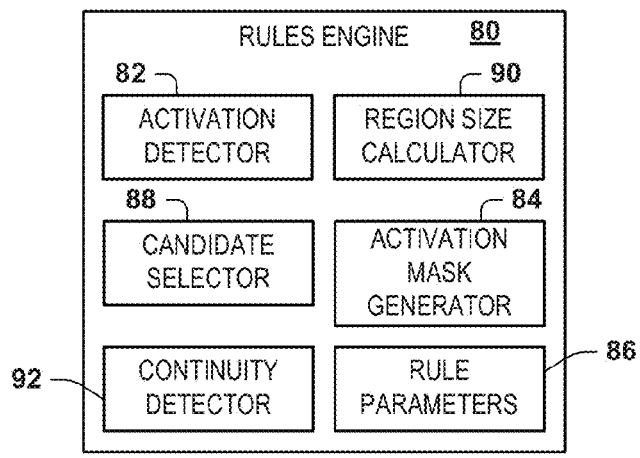
FIG. 4 depicts an example of a rules engine that can be implemented to control focal detection.

An example of a rules engine 80 that can implement additional rules to improve sensitivity and/or specificity for the focal point detection is demonstrated in FIG. 4. The rules engine 80 can correspond to and be implemented as the rules engine 24 of FIG. 1, and reference can be made back to FIG. 1 for additional context.

The rules engine 80 can be programmed to include analytics, logic and parameter data for implementing a variety of rules to provide enhanced specificity and/or sensitivity for use in detecting one or more focal points from electrical activity (e.g., based on measured electrical potentials) distributed across a geometric surface for patient anatomy (e.g., the heart or other tissue). In conjunction with the focal detection function 20 of FIG. 1 disclosed above, the rules engine 80 can mitigate false positive detection as well as false negative detections. The rules engine 80 can thus be implemented as machine readable instructions that can be stored in one or more non-transitory media and be executed by a processing resource (e.g., one or more processor cores) of one or more computers. An example of a method that can correspond to the machine readable instructions implemented as the rules engine 80 is demonstrated in FIG. 9.

In the example of FIG. 4, the rules engine 80 includes an activation detector 82 that is programmed to detect activation for each node on the geometric surface. For example, the activation detector 82 can be programmed to detect activation as beginning at a chosen phase value ($\theta 1$) and mark the node as being ON or activated until the phase changes to another chosen phase value ($\theta 2$, where $\theta 1 \neq \theta 2$). As an example, $\theta 2$ can be selected automatically as a time when activation for the node has been determined to end. In other examples, $\theta 2$ can be selected to provide a predetermined activation time (e.g., $\theta 2 - \theta 1$=a fixed time interval). The values of $\theta 1$ and $\theta 2$ can be programmed in response to a user input and can vary depending on how the phase calculator translates the electrical cycle for a given node into phase.

Figure 5:
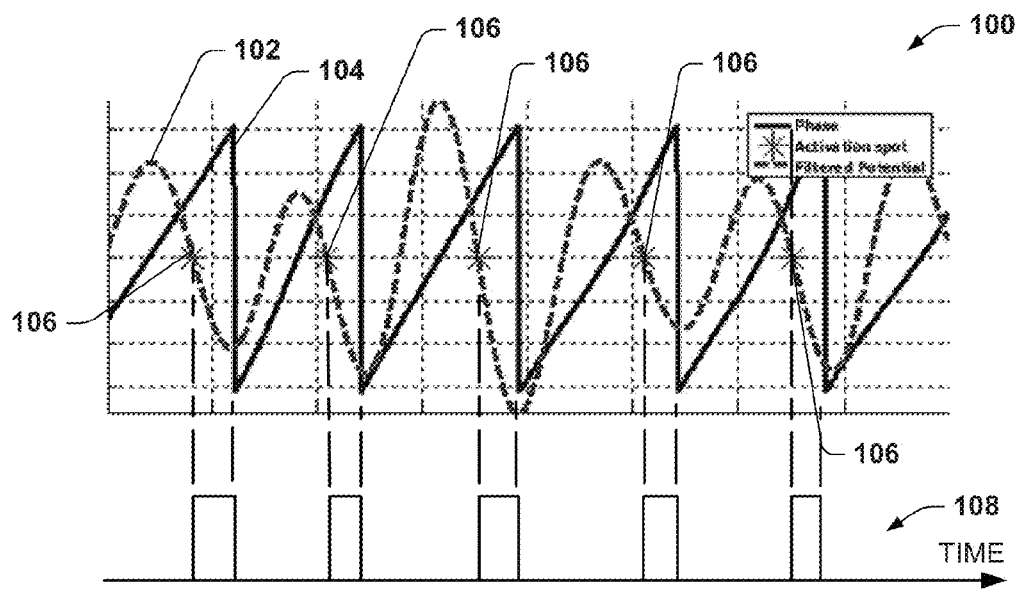
FIG. 5 depicts plots of signals that can be utilized to determine activation times.

FIG. 5 depicts an example of signal diagram 100 that includes a filtered electrical potential 102 for a given node and a corresponding phase 104 the given node. For example, the phase 104 can be calculated (e.g., by phase calculator 18 of FIG. 1) to represent the phase of the electrical signal for the given node. In the example of FIG. 5, activation begins at an activation spot 106, corresponding to when the phase has a value of $\theta 1$, and continues to when the computed phase value of the signal 104 changes to $\pi$. Thus the activation time for each cycle of the given node's phase 104 extends from the activation spot 106 to a time when the phase changes at $\theta 2$. The activation time for the signal can vary over time for each respective node, as illustrated by the activation coding demonstrated at 108. In other examples, the activation time interval can be a fixed time. For instance, the activation time interval for a given node can extend from a beginning time, such as when the phase has a value of $\theta 1$ to an end time following a fixed time window (e.g., about 50 ms). The activation detector 82 thus can generate activation coding 108 to encode the activation for each respective node over the surface of interest.

By way of further example, the activation coding 108 can be utilized to mark each respective node as activated (e.g., ON) between the starting and ending time indices and mark each node as deactivated (e.g., OFF) otherwise. This provides the example activation coding 108 for each node, such as shown in FIG. 5. Since each respective node across the surface can be coded as being ON or OFF over a time interval, a contiguous set of nodes that are concurrently ON for the geometric (e.g., cardiac) surface will form a region of activation, such as the changing growing region demonstrated in FIG. 6. The focal detection function can employ the rules engine 80 to determine whether or not each respective node is a focal point, as disclosed herein.

The rules engine 80 can also include rule parameters 86 that can be utilized by the components of the rules engine 80 (and focal detection function 22 of FIG. 1) to implement the logic and analytics disclosed herein. For instance, the rule parameters 86 can specify values to set one or more thresholds and other parameters that can control the focal detection process. The rule parameters can be stored in memory, and may be fixed values or may be programmable in response to a user input.

An activation mask generator 84 can be programmed to generate one or more activation masks. For example, the activation mask generator 84 can generate an activation coding mask, such as corresponding to the activation coding 108 of FIG. 5, to mark the beginning and end of each activation for a given node. In other examples, a fixed time from each initial activation on-time can be used to configure the mask. The corresponding activation mask can be generated for each respective candidate node on the geometric surface. Additionally, the activation mask generator 84 can provide a magnitude activation mask, such as by setting a minimum magnitude threshold (e.g., in a range from about 0.01 mV to about 0.1 mV) for the electrical signals for each node.

The rules engine 80 can include a candidate selector 88 that is programmed to apply each mask that was generated by the activation mask generator 84 to identify a set of focal candidates across the geometric surface of interest. The set of focal candidates can be a proper subset of the total set of nodes across the geometric surface. For example, the candidate selector can employ combinational logic (e.g., a logical AND function) to phase and potential signals for each node for identifying focal candidate nodes. As described herein, in some examples, the geometric surface of interest can include a particular region of interest or it can include an entire surface of the heart.

The identified focal candidates thus can be stored in memory as a set of prospective candidates meeting the initial criteria established by the masks. In some examples, this may include the direct phase comparisons disclosed with respect to FIG. 1. Each of the focal candidates thus can be evaluated by the rules engine 80 in conjunction with the focal detection function (focal detection 20 of FIG. 1) to determine whether or not each of the respective candidate node is a focal point.

As a further example, the rules engine 80 can include a region size calculator 90 can be programmed to determine the size of a region that has been activated (e.g., one or more nodes distributed across the surface) at a given time interval for a given candidate. The activation for each such node can be determined by the activation detector 82, as mentioned above. For example, at or near (e.g., within one or two intervals from) an initial activation time for a given node (e.g., corresponding to the time of activation at activation spot 106 of FIG. 5), the rules engine 80 can ascertain whether the initial size of the activated region exceeds a maximum initial size threshold (e.g., set by rule parameters 86). The maximum initial size can be used to determine whether the candidate may be a focal point or not. For example, if the maximum initial size is exceeded, it can be ascertained that the respective candidate is not a focal point. The rules engine 80 further can add one or more subsequent time frames in the sample to continue adding one or more nodes that may be activated at a time following the initial activation of the given candidate node that is being evaluated by the rules engine 80. The region size calculator 90 can in turn determine if the additional activations for one or more other nodes has affected the size of the activated region. This can be utilized to determine whether the size of the activation region has grown or otherwise changed size over a predetermined period of time, such as a plurality of intervals. The absence of changes in size over such time period can help classify the candidate as not being a focal trigger.

The rules engine 80 can also include a continuity detector 92 that is programmed to ascertain whether the set of nodes forming the activated region are a contiguous set of nodes in a given neighborhood. The continuity detector 92 can evaluate a spatial and/or temporal continuity to determine if the current activation region is connected with the earlier activation for the given candidate node. If the following activation region is not connected with the earlier activation, the focal detection function can determine that the candidate node is not a focal point, such as if its size does not change (or shrinks) over time.

The rules engine 80 can also employ the regions size calculator 90 to determine if at or near the end of the activation time, the activated region is larger than a threshold minimum final size, such as can be set by the rules parameter 86. The minimum final size can be a fixed value or be user programmable (e.g., in response to a user input). The focal detection function thus can employ the rules engine 80 to determine whether or not each of the nodes is a focal point. The results, including the final results as well as at intermediate stages, can be stored in memory as focal data and used to generate one or more graphical maps, such as disclosed herein.

Figure 6:
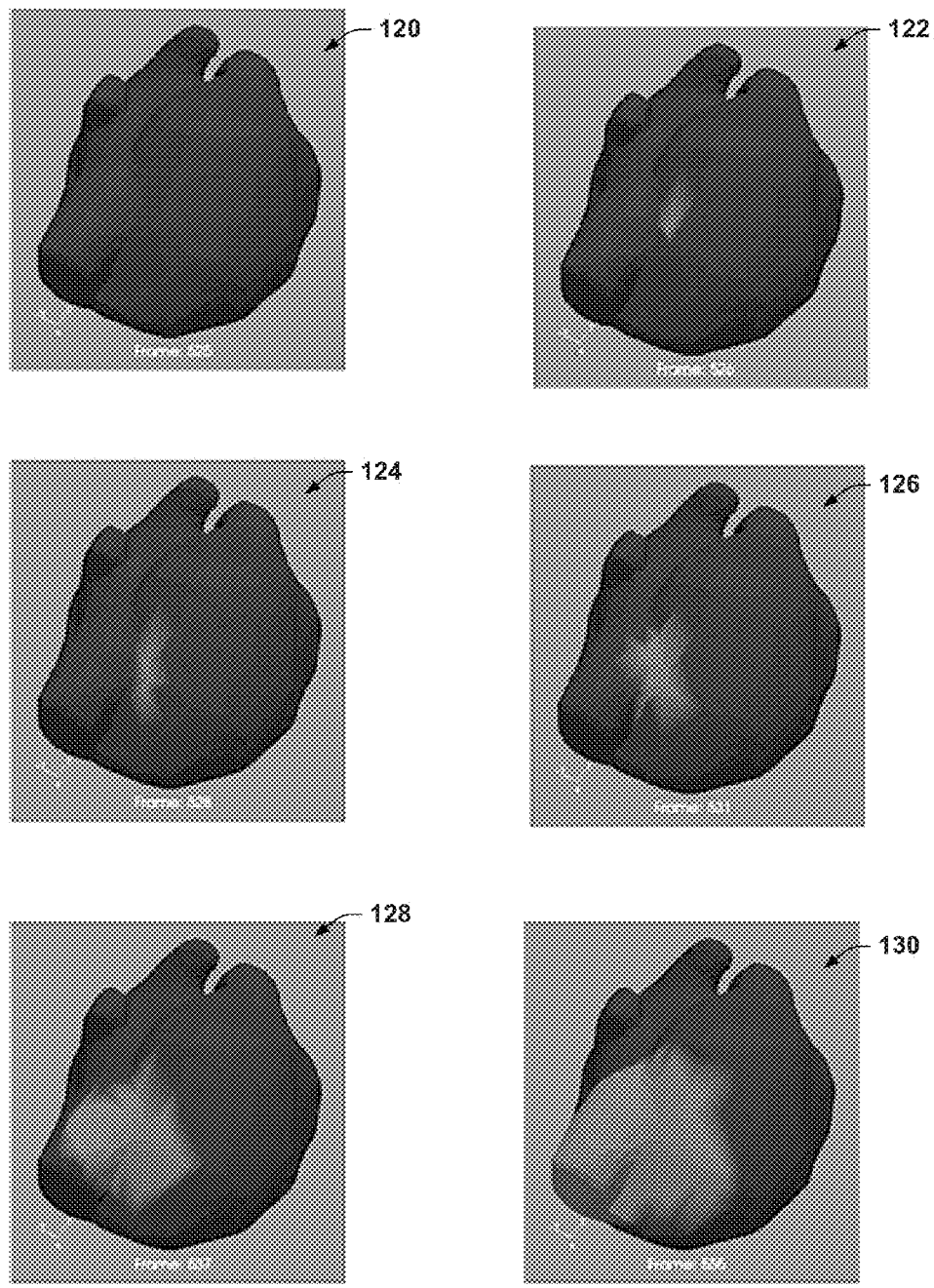
FIG. 6 depicts graphical maps demonstrating a growing focal region over time.

FIG. 6 depicts an example of multiple time frames demonstrating how activation from one spot can trigger activation in surrounding nodes that grows over time from the initial trigger across the geometric surface of a patient's heart. The example of FIG. 6 demonstrates six different time frames demonstrated at 120, 122, 124, 126, 128 and 130 (e.g., ranging over about 30 ms). Each of the respective time frames correspond to different instances in time during activation of a given candidate focal node. As demonstrated in the focal point maps 120, 122, 124, 126, 128 and 130, it is demonstrated that activation initiates at a given spot or region such as corresponding to one or more nodes on the surface in map 120 then forms a small island, as demonstrated at 122 through 124, and continues to spread and grow as demonstrated at 126 through 130. As demonstrated in FIG. 6, the spreading of activation from a focal point can be anisotropic.

Figure 7:
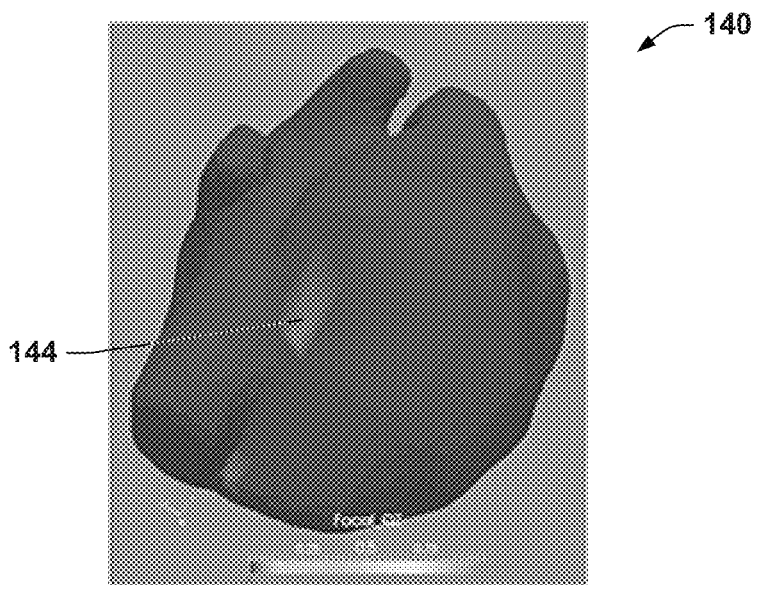
FIG. 7 depicts an example of a graphical map demonstrating a detected focal point.

FIG. 7 depicts an example of an electrophysiological map 140 demonstrating a focal trigger 144 (e.g., one or more nodes) that can be generated by a map generator (e.g., map generator 28 of FIG. 1). The focal trigger in the example of FIG. 7 can be detected (e.g. by focal detection function 20 of FIG. 1) based on applying rules during the growth of the focal region demonstrated in the example of FIG. 6 over a given interval.

Figure 8:
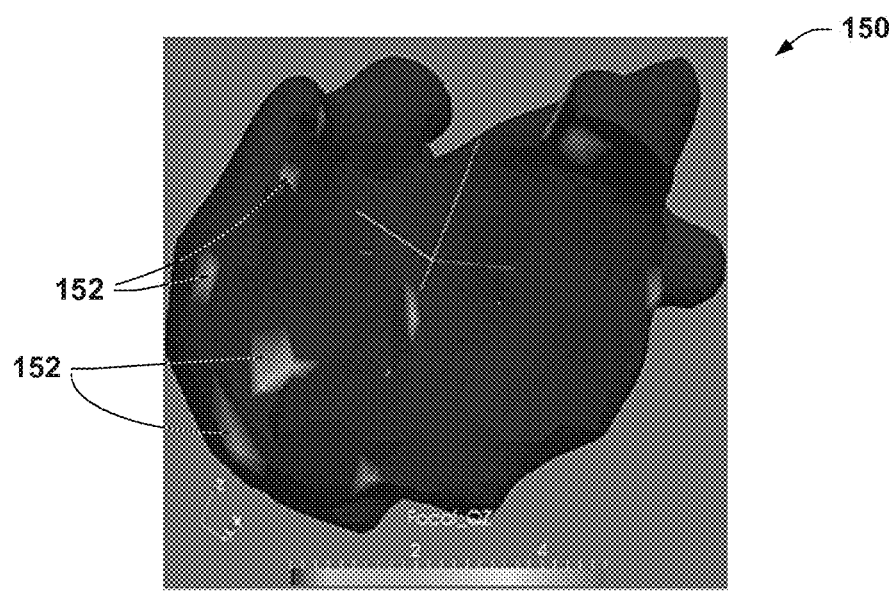
FIG. 8 depicts an example of a graphical map demonstrating focal points over multiple intervals.

FIG. 8 depicts of an electrophysiological map 150 that can be generated by a map generator (e.g., map generator 28 of FIG. 1). The electrophysiological map 150 includes a plurality of focal points 152 detected for on a plurality of different intervals. For instance the focal points can be detected based on application of the rules engine by the focal detection function as disclosed herein.

Figure 9:
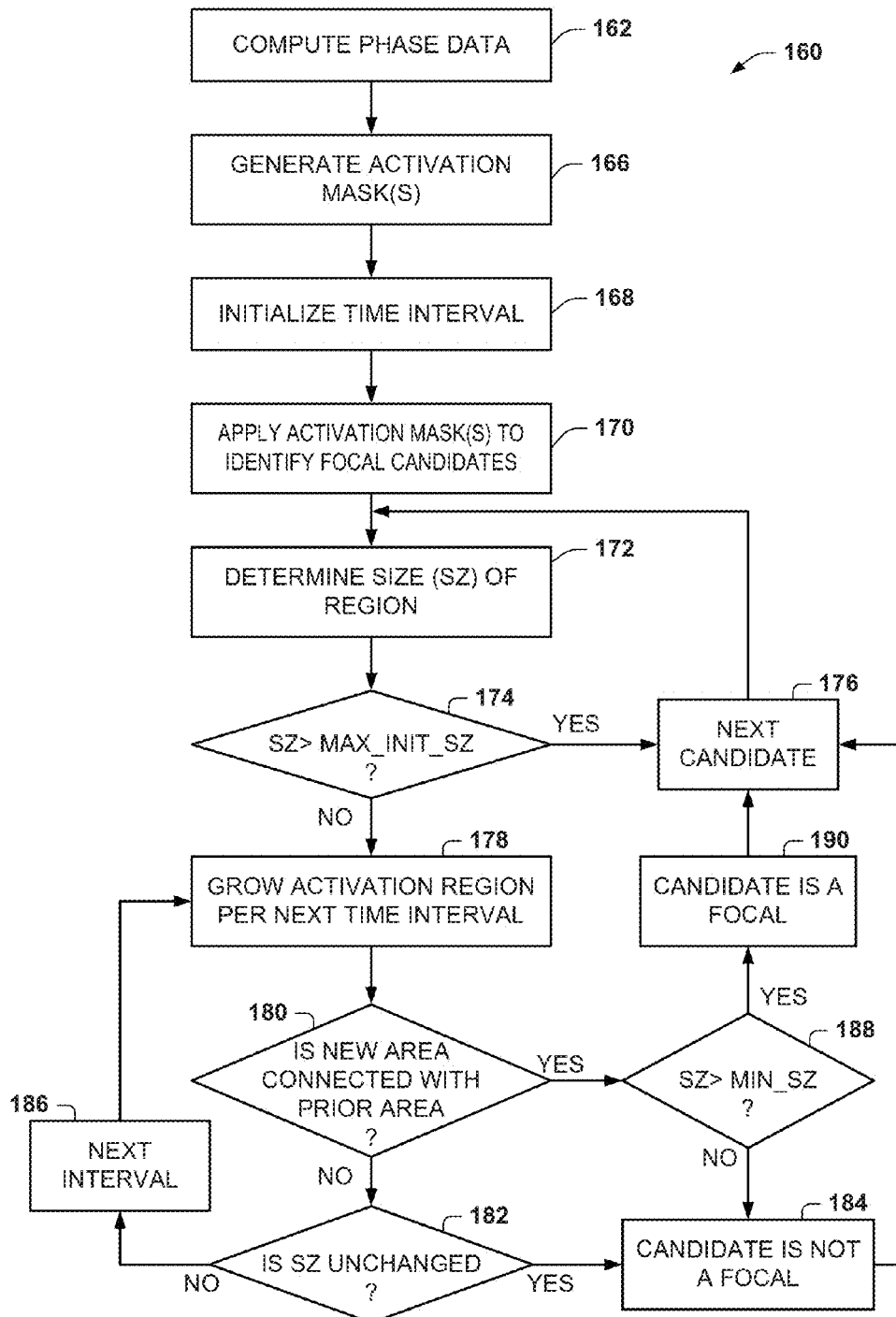
FIG. 9 is a flow diagram demonstrating a method for identifying focal points.

In view of the foregoing structural and functional features described above, methods that can be implemented will be better appreciated with reference to FIG. 9. While, for purposes of simplicity of explanation, the method of FIG. 9 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method. The methods or portions thereof can be implemented as instructions stored in one or more non-transitory storage media as well as be executed by a processor of a computer device, for example.

FIG. 9 depicts a flow diagram demonstrating an example method for identifying one or more focal points. The method 160 can be implemented by the focal detection function and rules engine disclosed herein (e.g., focal detection function 20 and rules engine 24 of FIG. 1 or rules engine 80 of FIG. 4). At 162, phase data is computed based on a sampling interval over a period of time, which may be selected by a user in response to a user input or be automatically detected.

At 166, one or more activation masks can be generated (e.g., by mask generator 84 of FIG. 4) based on the phase information computed at 162. For instance, one activation mask can encode activation temporal, such as the beginning and end time of activation for each respective node such as beginning at a time when the phase has a value of θ1 and an ending time. The ending time can be determined when the phase has a value of θ2 or it can establish a fixed time period for the activation time from the detected beginning. Time indices can be set to correspond to each of the starting and end times for each activation time period. Another mask can be generated to set a minimum threshold magnitude for the sensed electrical signal at each node (e.g., a filtered or processed electrical potential). The generated masks and associated thresholds can be stored as parameters (e.g., rule parameters 86 of FIG. 4) in corresponding memory. The time interval for analyzing the phase values and activation can be set and initialized at 168. This time interval can range anywhere from a selected portion of a sampling interval for which the phase data is computed at 162 up to an entire length of one or more sampling intervals.

At 170, the activation masks that are applied to the phase data to identify a set of focal candidates for further evaluation (e.g., corresponding to candidate selector 88 of FIG. 4). Each of the nodes corresponding to the focal candidates thus can be stored in memory for use in performing the remaining portion of the method 160 with respect to each respective candidate. At 172 a size of the region can be determined (e.g., by region size calculator 90 of FIG. 4) for an initial activation time period (e.g., a second interval of activation for the candidate node). At 174, a determination can be made as to whether the determined size is greater than a maximum initial size. If the size of the initial region is determined to exceed the maximum initial size, the method proceeds to 176 in which a next candidate node is selected (e.g., by candidate selector 88 of FIG. 4) for processing. This can correspond to an example where an initial region is too large such that it is too difficult to ascertain which node or set of nodes corresponds to a trigger. From 176 the method returns to 172 to process the next candidate that has been selected.

If at 174, the size does not exceed the maximum initial size for the corresponding candidate, the method can proceed to 178. At 178 the method grows the activation region for a next time intervals. For example, a time interval can correspond to a time when each sample of electrical information is measured, such as ranging from 0.5 to about 2 ms. At 180 a determination is made (e.g., by continuity detector 92 of FIG. 4) whether the region that is activated for the next time interval is connected with the prior region that was activated (in the previous time interval). This determination at 180 thus can consider temporal and/or spatial connections, such as to confirm whether the newly activated area was triggered by the proceeding activation area. If the new area is not connected with the prior area, the method proceeds to 182.

At 182, a determination is made as to whether the determined size remains unchanged over a predetermined period of time. For example, the method can determine whether the size remains unchanged over a time interval (e.g., 4 ms). If the size remains unchanged over this time period such as expanding multiple intervals, the method proceeds to 184 to identify the candidate node as not being a focal point. From 184 the method can proceed to 176 to process the next candidate node from the set of candidates identified at 170. If at 182 it is determined that the size has changed, the method can proceed to 186 to increment to a next time interval and the method can continue to 178 to grow the corresponding activation region for such next interval.

Returning back to 180 if it is determined that the newly activated area is connected with the prior area (e.g., temporary and/or spatially), the method can proceed to 188. At 188, a determination can be made as to whether a size exceeds a minimum final size if the aggregate size of the activated region does not exceed the minimum final size the method proceeds to 184 in which the candidate can be marked as not being a focal point. However, if the size exceeds the minimum final size the method can proceed to 190 in which the candidate can be identified as a focal point.

From 190, the method can proceed to 176 to process the next focal candidate. As mentioned, the method 160 can be repeated for each candidate focal point over the time interval initialized at 168. For instance, the method 160 can loop from 172 to 190 for each respective candidate. Additionally, the method can further loop from 168 to 190 for each respective time frame (e.g., interval) that is being processed. In this way, the method 160 can identify different focal points over different time intervals. The identified focal points further can be aggregated and utilized to generate a corresponding focal point map (e.g., map generator 28 of FIG. 1), such as shown in FIG. 8.

Figure 10:
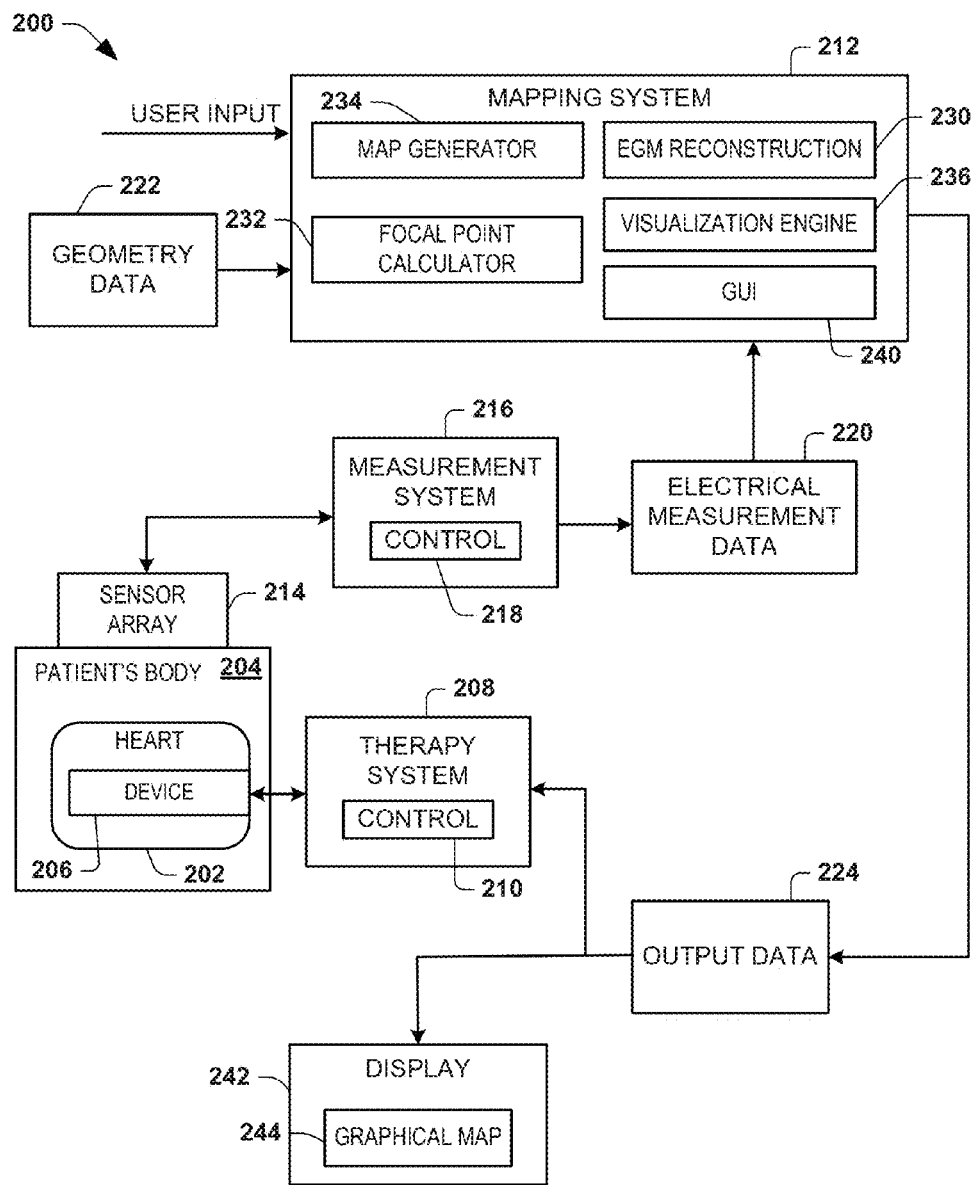
FIG. 10 depicts an example of a system that can be implemented for diagnosis and therapy delivery.

FIG. 10 depicts an example of a system 200 that can be utilized for performing diagnostics and/or treatment of a patient. In some examples, the system 200 can generate focal point maps for the heart 202 in real time as part of a diagnostic procedure (e.g., an electrophysiology study) to help assess the electrical activity and conduction pathways of a patient's heart.

Additionally or alternatively, the system 200 can be utilized as part of a treatment procedure such as to help a physician determine parameters for delivering a therapy to the patient (e.g., delivery location, amount and type of therapy). For example, a catheter, such as a pacing catheter, having one or more therapy delivery devices 206 affixed thereto can be inserted into the body 204 as to contact the patient's heart 202, endocardially or epicardially. Those skilled in the art will understand and appreciate various type and configurations of therapy delivery devices 206 that can be utilized, which can vary depending on the type of treatment and the procedure. For instance, the therapy device 206 can be configured to deliver electrical therapy, chemical therapy, sound wave therapy, thermal therapy or any combination thereof.

By way of example, the therapy delivery device 206 can include one or more electrodes located at a tip of an ablation catheter configured to generate heat for ablating tissue in response to electrical signals (e.g., radiofrequency energy) supplied by a therapy system 208. In other examples, the therapy delivery device 206 can be configured to deliver cooling to perform ablation (e.g., cryogenic ablation), to deliver chemicals (e.g., drugs), ultrasound ablation, high-frequency ablation, or a combination of these or other therapy mechanisms. In still other examples, the therapy delivery device 206 can include one or more electrodes located at a tip of a pacing catheter to deliver electrical stimulation, such as for pacing the heart, in response to electrical signals (e.g., pacing pulses) supplied by a therapy system 208. Other types of therapy can also be delivered via the therapy system 208 and the invasive therapy delivery device 206 that is positioned within the body.

The therapy system 208 can be located external to the patient's body 204 and be configured to control therapy that is being delivered by the device 206. For instance, the therapy system 208 includes control circuitry 210 that can communicate (e.g., supply) electrical signals via a conductive link electrically connected between the device (e.g., electrodes) 206 and the therapy system 208. The control system 210 can control parameters of the signals supplied to the device 206 (e.g., current, voltage, repetition rate, trigger delay, sensing trigger amplitude) for delivering therapy (e.g., ablation or stimulation) via the electrode(s) 204 to one or more location of the heart 202. The control circuitry 210 can set the therapy parameters and apply stimulation based automatic, manual (e.g., user input) or a combination of automatic and manual (e.g., semiautomatic) controls. Output data 224, including data identifying one or more focal points, can also be provided to the therapy system 208 for implementing such controls. One or more sensors (not shown) can also communicate sensor information back to the therapy system 208. The position of the device 206 relative to the heart 202 can be determined and tracked intraoperatively via an imaging modality (e.g., fluoroscopy, xray), a mapping system 212, direct vision or the like. The location of the device 206 and the therapy parameters thus can be combined to provide corresponding therapy parameter data.

Before, during and/or after providing a therapy via the therapy system 208, another system or subsystem can be utilized to acquire electrophysiology information for the patient. In the example of FIG. 10, a sensor array 214 includes one or more electrodes that can be utilized for recording patient activity. The sensor array can be position non-invasively on the patient's body and/or it can be position invasively in the body to measure patient electrical activity.

As one example, the sensor array 214 can correspond to a high-density arrangement of body surface sensors (e.g., greater than 200 electrodes) that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, filed 10 Nov. 2009, which is incorporated herein by reference. Other arrangements of sensing electrodes can be used as the sensor array 214. The array can be a reduced set of electrodes, which that does not cover the patient's entire torso and is designed for measuring electrical activity for a particular purpose (e.g., an array of electrodes specially designed for analyzing AF and/or VF) and/or for monitoring a predetermined spatial region of the heart.

One or more sensors may also be located on the device 206 that is inserted into the patient's body. Such electrode can be utilized in conjunction with the sensor array 214 for mapping electrical activity for an endocardial surface, such as the wall of a heart chamber, as well as for an epicardial surface. Additionally, such electrode can also be utilized to help localize the device 206 within the heart 202, which can be registered into an image or map that is generated by the system 200. Alternatively, such localization can be implemented in the absence of emitting a signal from an electrode within or on the heart 202.

In each of such example approaches for acquiring patient electrical information, including invasively, non-invasively, or a combination of invasive and non-invasive sensors, the sensor array(s) 214 provide the sensed electrical information to a corresponding measurement system 216. The measurement system 216 can include appropriate controls and signal processing circuitry 218 for providing corresponding measurement data 220 that describes electrical activity detected by the sensors in the sensor array 214. The measurement data 220 can include analog or digital information.

The control 218 can also be configured to control the data acquisition process for measuring electrical activity and providing the measurement data 220. The measurement data 220 can be acquired concurrently with the delivering therapy by the therapy system, such as to detect electrical activity of the heart 202 that occurs in response to applying a given therapy (e.g., according to therapy parameters). For instance, appropriate time stamps can be utilized for indexing the temporal relationship between the respective data 220 and therapy parameters to facilitate the evaluation and analysis thereof.

The mapping system 212 is programmed to combine the measurement data 220 corresponding to electrical activity of the heart 202 with geometry data 222 by applying appropriate processing and computations to provide corresponding output data 224. The output data 224 can be represent or characterize one or more focal points across a geometric surface (e.g., a cardiac envelope or other surface associated with the heart 202).

Since the measurement system 216 can measure electrical activity of a predetermined region or the entire heart concurrently (e.g., where the sensor array covers the entire thorax of the patient's body 204) the resulting output data 224 thus can also represent concurrent data for the predetermined region or the entire heart in a temporally and spatially consistent manner. This can include concurrent measurements for the both atria and/or both ventricles. The time interval for which the output data/maps are computed can be selected based on user input. Additionally or alternatively, the selected intervals can be synchronized with the application of therapy by the therapy system 208.

For the example where the electrical measurement data is obtained non-invasively (e.g., via body surface sensor array 214), electrogram reconstruction 230 can be programmed to compute an inverse solution and provide corresponding reconstructed electrograms based on the process signals and the geometry data 222. The reconstructed electrograms thus can correspond to electrocardiographic activity across a cardiac envelope, and can include static (three-dimensional at a given instant in time) and/or be dynamic (e.g., four-dimensional map that varies over time). Examples of inverse algorithms that can be utilized in the system 10 are disclosed in U.S. Pat. Nos. 7,983,743 and 6,772,004, which are incorporated herein by reference. The EGM reconstruction 230 thus can reconstruct the body surface electrical activity measured via the sensor array 214 onto a multitude of locations on a cardiac envelope (e.g., greater than 1000 locations, such as about 2000 locations or more). In other examples, the mapping system 212 can compute electrical activity over a region of the heart based on electrical activity measured invasively, such as via a basket catheter or other form of measurement probe.

As disclosed herein, the cardiac envelope can correspond to a three dimensional surface geometry corresponding to a patient's heart, which surface can be epicardial or endocardial. Alternatively or additionally, the cardiac envelope can correspond to a geometric surface that resides between the epicardial surface of a patient's heart and the surface of the patient's body where the sensor array 214 has been positioned. Additionally, the geometry data 222 that is utilized by the electrogram reconstruction 230 can correspond to actual patient anatomical geometry, a preprogrammed model or a combination thereof (e.g., a model that is modified based on patient anatomy).

As an example, the geometry data 222 may be in the form of a three-dimensional graphical representation of the patient's torso, such as image data acquired for the patient.

Such image processing can include extraction and segmentation of anatomical features, including one or more organs and other structures, from a digital image set. Additionally, a location for each of the electrodes in the sensor array 214 can be included in the geometry data 222, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array, such as a digitizer.

Alternatively or additionally, the geometry data 222 can correspond to a mathematical model, such as can be a generic model or a model that has been constructed based on image data for the patient. Appropriate anatomical or other landmarks, including locations for the electrodes in the sensor array 214 can be identified in the geometry data 222 to facilitate registration of the electrical measurement data 220 and performing the inverse method thereon. The identification of such landmarks can be done manually (e.g., by a person via image editing software) or automatically (e.g., via image processing techniques).

By way of further example, the geometry data 222 can be acquired using nearly any imaging modality based on which a corresponding representation can be constructed, such as described herein. Such imaging may be performed concurrently with recording the electrical activity that is utilized to generate the patient measurement data 220 or the imaging can be performed separately (e.g., before the measurement data has been acquired).

Following (or concurrently with) determining electrical potential data (e.g., electrogram data computed from non-invasively and/or invasively acquired measurements) across the geometric surface of the heart, the electrogram data can further undergo signal processing to compute one or more cardiac maps. The mapping system 212 can include a focal point calculator 232 that can be programmed to compute focal point data for each of a plurality of points in the given spatial region based on the geometry and electrical measurement data. For example, the focal point can be programmed to compute phase for nodes distributed across a given geometric surface of the patient's heart, such as disclosed herein. The focal point calculator 232 can also compute focal point data based on comparing phase information of a given vertex node relative to the phase of each of its neighboring nodes. The comparison can be performed for the vertex node and each node in one or more layers (see, e.g., FIG. 2). A score can be assigned to one of the given node and its neighboring node based on each comparison. The score can be a fixed value or it may vary as disclosed herein. The comparing and scoring can be repeated for each of the nodes to provide corresponding focal point map data, demonstrated as output data 224.

As a further example, the focal point calculator 232 can include a rules engine (e.g., rules engine 80) programmed to apply one or more rules to increase the sensitivity and specificity of the focal point analysis. For instance, the rules engine can employ parameters that can be set to control the focal analysis for each candidate node over a set of one or more intervals, such as disclose with respect to the method FIG. 9. The focal point calculator 232 thus can provide a set of one or more focal points as part of output data 224 for each of the time intervals that are analyzed based on the electrical measurement data sensed for the patient.

The output data 224 can be employed by a display 242 to render a graphical map representation 244. Parameters associated with the generation of the focal point map or other aspects of visualization, such as including selecting one or more time intervals, setting one or more thresholds, the type of information that is to be presented in the graphical map and the like, can be selected in response to a user input via a corresponding visualization GUI 190, for example. The mapping system 224 thus can generate corresponding output data 224 that can in turn be rendered by the visualization engine as a corresponding graphical output in a display 192, such as including an electrocardiographic focal point map 194.

In addition to the mapping system 212 generating one or more focal point maps, other types of electrocardiographic mapping can be implemented such as including activation maps, dominant frequency maps and the like. For example, the display 192 can include one or more regions for displaying composite singularity map data concurrently with corresponding activation or dominant frequency maps to facilitate diagnosis and treatment of AF or VF.

Additionally, the output data 224, including information about the size and location of the focal points determined from the focal point map, can be provided to the therapy system 208. The control 210 of the therapy system can utilize the output data to control one or more therapy parameters. As an example, the control 210 can control delivery of ablation therapy to a site of the heart (e.g., epicardial or endocardial wall) based on the location and size of a phase singularity determined from a composite phase singularity map. Other types of therapy can also be controlled based on the output data. The control that is implemented can be fully automated control, semi-automated control (partially automated and responsive to a user input) or manual control based on the output data 224.

As a further example, the focal point detection approach, as disclosed herein, can be combined with other arrhythmia detection and mapping approaches as part of an integrated system (e.g., the system 200). For example, the focal point detection can be combined with phase singularity detection that is disclosed in the above-incorporated PCT Application No. PCT/US13/60851.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware, such as shown and described with respect to the computer system of FIG. 11. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 11:
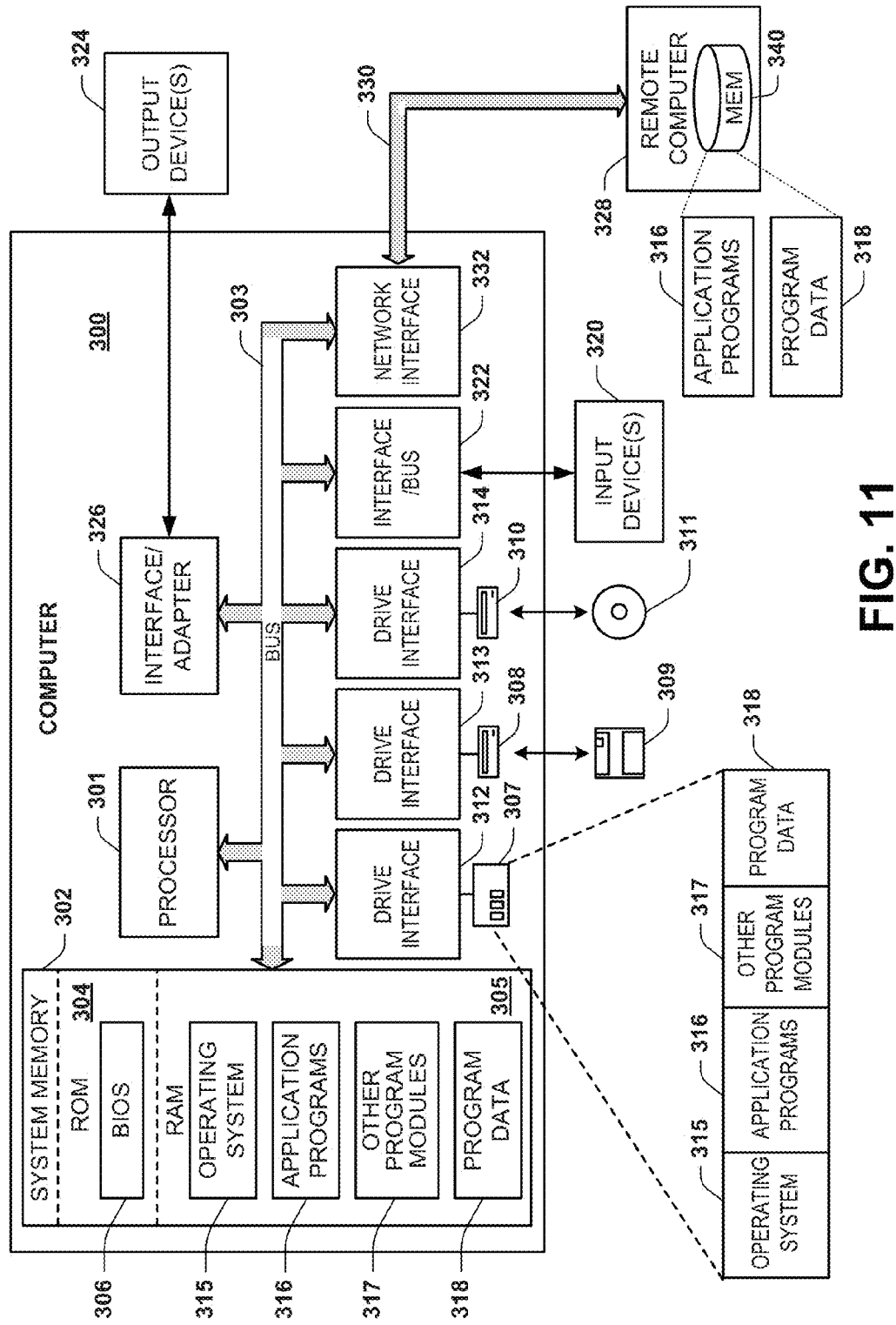
FIG. 11 depicts an example computing environment.

In this regard, FIG. 11 illustrates one example of a computer system 300 that can be employed to execute one or more embodiments, such as including acquisition and processing of sensor data, processing of image data, as well as analysis of transformed sensor data and image data associated with the analysis of cardiac electrical activity. Computer system 300 can be implemented on one or more general purpose networked computer systems, embedded computer systems, routers, switches, server devices, client devices, various intermediate devices/nodes or stand alone computer systems. Additionally, computer system 300 can be implemented on various mobile clients such as, for example, a personal digital assistant (PDA), laptop computer, pager, smart phone and the like, provided it includes sufficient processing capabilities.

Computer system 300 includes processing unit 301, system memory 302, and system bus 303 that couples various system components, including the system memory, to processing unit 301. Dual microprocessors and other multi-processor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the systems and method disclosed herein.

A number of program modules may be stored in drives and RAM 305, including operating system 315, one or more application programs 316, other program modules 317, and program data 318. The application programs and program data can include functions and methods programmed to acquire, process and display electrical data from one or more sensors, such as shown and described herein. The application programs and program data can include functions and methods programmed to process signals and compute a phase data and identify one or more focal points as disclosed herein. The application programs and program data can also include functions and methods programmed to generate one or more focal point graphical maps as disclosed herein.

A user may enter commands and information into computer system 300 through one or more input devices 320, such as a pointing device (e.g., a mouse, touch screen), keyboard, microphone, joystick, gesture control, game pad, scanner, and the like. For instance, the user can employ input device 320 to edit or modify a domain model. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A system comprising:
   memory to store data and machine readable instructions;
   a processor to access the memory and execute the machine readable instructions, the machine readable instructions comprising:

a phase calculator programmed to compute phase values for electrical signals at each of a plurality of nodes distributed across a geometric surface corresponding to patient tissue;

a mask generator programmed to generate an activation mask for a given node of the plurality of nodes specifying a set of at least one activation time period having a beginning time and an ending time, the beginning time corresponding to when a phase value of a signal at the least one of the plurality of nodes has a given value and the ending time corresponding to when the phase value of the signal at the least one of the plurality of nodes has another value;

a candidate selector programmed to apply the activation mask to the computed phases values computed for each of the plurality nodes on the geometric surface to identify a set of focal candidate nodes;

a focal detector programmed to analyze the set of focal candidate nodes to identify a given focal candidate node corresponding to a spatial location of a focal point for the geometric surface, the focal detector further programmed to generate focal point data characterizing the identified given focal candidate node; and a map generator programmed to generate a graphical map representing the focal point detected on the geometric surface based on the focal point data; and a display to receive and display the generated graphical map to visualize the focal point detected on the geometric surface.

2. The system of claim 1, wherein the focal detector further comprises an activation detector programmed to determine the activation time interval for at least a substantial portion of the plurality of nodes.

3. The system of claim 2, wherein the activation mask is a temporal activation mask, the mask generator further to provide a magnitude activation mask that specifies a minimum magnitude for the electrical signals at each of the plurality of nodes on the geometric surface, and wherein the candidate selector is programmed to identify the set of focal candidate nodes in response to applying both the temporal activation mask to the computed activation time intervals for each of the plurality of nodes and the magnitude activation mask to the electrical signals at each of the plurality of nodes.

4. The system of claim 2, wherein the focal detector further comprises:

a size calculator programmed to compute a size of an activation region across the geometric surface according to which of the plurality of nodes are activated for a respective activation time in a corresponding time interval, and wherein the focal detector is further programmed to determine whether or not each given focal candidate node is a focal point based on the computed size of the activation region for at least one time interval.

5. The system of claim 4, wherein the focal detector further comprises:

a continuity detector programmed to provide continuity data to indicate if newly activated nodes for at least one other activation interval following the respective activation time interval are connected with the activation region that was activated for the respective activation time period, wherein the focal detector is to determine that each given focal candidate node is a focal point based on the continuity data and based on the computed size of the activation region for the other activation time exceeding a minimum size parameter.

6. The system of claim 5, wherein the focal detector is further programmed to determine that one of the given candidate nodes is not a focal point based on the continuity data indicating that newly activated nodes for at least one other activation interval following the respective activation time interval are unconnected with the activation region that was activated for the respective activation time period and the computed size has not changed over a predetermined time period.

7. The system of claim 1, wherein the geometric surface comprises one of an epicardial surface, an endocardial surface or another cardiac envelope.

8. The system of claim 7, further comprising:

a measurement system configured to measure non-invasively electrical activity for the geometric surface of the patient and provide corresponding electrical measurement data;

wherein the machine instructions further comprise a reconstruction function programmed to solving an inverse problem to compute reconstructed electrical signals, which correspond to the electrical signals, for each of the nodes on the geometric surface based on electrical measurement data and geometry data, the phase value for each of the plurality of nodes being computed based on the reconstructed electrical signals for the respective nodes.

9. The system of claim 1, further comprising a measurement system configured to measure invasively electrical activity for the geometric surface, wherein the electrical signals for each of the plurality of nodes are derived based on the invasively measured electrical activity.

10. The system of claim 1, further comprising a therapy system to control delivery of a therapy to a selected location on the geometric surface based on the focal point data.

11. A non-transitory computer-readable medium having instructions executable by a processor for performing a method, the method comprising:

computing phase values for signals of each of a plurality of nodes on a geometric surface region associated with tissue of a patient, a subset of the nodes surrounding a given node of the plurality of nodes defining neighboring nodes of the given node;

generating an activation mask for the given node based on an activation detected for at least one of the plurality of nodes, the activation mask specifying a set of at least one activation time period having a beginning time and an ending time, the beginning time corresponding to when phase value of a signal at the least one of the plurality of nodes has a given value and the ending time corresponding to when the phase value of the signal at the least one of the plurality of nodes has another value;

applying the activation mask to the computed phases values computed for each of the plurality nodes on the geometric surface region to identify a set of focal candidate nodes;

analyzing the set of focal candidate nodes to identify a given focal candidate node corresponding to a spatial location of a focal point for the geometric surface region;

generating focal point data characterizing the spatial location of the focal point; and providing a graphical map to a display to visualize the focal point for the geometric surface region based on the focal point data.

12. The medium of claim 11, wherein the ending time is a predetermined phase value that is fixed time from the beginning time.

13. The medium of claim 11, wherein the neighboring nodes comprise an arrangement of nodes having a plurality of layers that provide a neighborhood of the nodes relative to the given node.

14. The medium of claim 13, wherein the number of layers for each neighborhood is a programmable parameter.

15. The medium of claim 11, wherein the method further comprises detecting the activation for at least a substantial portion of the plurality of nodes.

16. The medium of claim 11, wherein the activation mask is a temporal activation mask,
wherein generating the activation mask further comprises setting a magnitude threshold that specifies a minimum magnitude for the signals at each of the plurality of nodes on the geometric surface region,
wherein the set of focal candidate nodes is identified in response to applying both the temporal activation mask and the magnitude threshold.

17. The medium of claim 11, further comprising:
computing a size of an activation region across the geometric surface region according to which of the plurality of nodes are activated for a respective activation time in a corresponding time interval, and
determining whether or not each given candidate node is a focal point based on the computed size of the activation region for at least one time interval.

18. The medium of claim 14, the determining further comprising:
detecting that a respective one of the given candidate nodes is a focal point if newly activated nodes for at least one other activation period following the respective activation time period are connected with the activation region that is activated for the respective activation time period and if the computed size of the activation region for the other activation time exceeds a minimum size parameter.

19. The medium of claim 17, determining that one of the given candidate nodes is not a focal point if nodes activated for a subsequent activation time are unconnected with the activation region that is activated for the respective activation time and the computed size has not changed over a predetermined time period.

20. The medium of claim 11, wherein the geometric surface region comprises one of an epicardial surface, an endocardial surface or another cardiac envelope.

21. The medium of claim 11, wherein the method further comprises solving an inverse problem to compute reconstructed electrical signals as the signals for each of the nodes on the geometric surface region based on electrical data acquired from the patient, the computed phase value for each of the nodes being computed based on the reconstructed electrical signals for the respective nodes.

22. The medium of claim 11, wherein the signals for each of the plurality of nodes are derived based on at least one of invasively acquired electrical data for the patient or non-invasively acquired electrical data for the patient.

23. A method comprising:
storing, in memory, electrical data representing electrical signals for a geometric surface corresponding to patient tissue;
computing, by a processor, phase values for the electrical signals at each of a plurality of nodes distributed across the geometric surface based on the electrical data;
generating, by the processor, an activation mask for the given node based on an activation detected for at least one of the plurality of nodes, the activation mask specifying a set of at least one activation time period having a beginning time and an ending time, the beginning time corresponding to when phase value of a signal at the least one of the plurality of nodes has a given value and the ending time corresponding to when the phase value of the signal at the least one of the plurality of nodes has another value;
applying, by the processor, the activation mask to the computed phases values computed for each of the plurality nodes on the geometric surface region to identify a set of focal candidate nodes;
analyzing, by the processor, a computed phase value of the given focal candidate node relative to computed phases values of the set of focal candidate nodes over an activation time period associated with the given focal candidate node;
determining, by the processor, if the given focal candidate node is the focal point based on the analyzing;
repeating the analyzing and determining for each focal candidate node to provide the focal point data specifying the spatial location corresponding to each focal point for the geometric surface region; and
providing, by the processor, a graphical map to a display to visualize the focal point for the geometric surface region based on the focal point data.

24. The system of claim 23, wherein the ending time is a fixed time from the beginning time.

* * * * *